United States Patent
von der Eltz et al.

(10) Patent No.: US 6,821,744 B2
(45) Date of Patent: Nov. 23, 2004

(54) METHOD, ASSAY, AND KIT FOR QUANTIFYING HIV PROTEASE INHIBITORS

(75) Inventors: Herbert von der Eltz, Weiheim (DE); Lili Arabshahi, Carmel, IN (US); Haijuan Li, Fishers, IN (US); Erasmus Huber, Finning (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 10/284,040

(22) Filed: Oct. 29, 2002

(65) Prior Publication Data

US 2004/0081957 A1 Apr. 29, 2004

(51) Int. Cl.[7] ............ G01N 33/53; C12Q 1/70; C12Q 1/06; C12N 5/16; C12N 1/00
(52) U.S. Cl. ............ 435/7.71; 435/5; 435/39; 435/7.4; 435/334; 435/339.1; 435/810
(58) Field of Search ............ 435/7.71, 5, 39, 435/7.4, 334, 339.1, 810

(56) References Cited

U.S. PATENT DOCUMENTS

| 4,480,042 A | 10/1984 | Craig et al. |
| 4,868,132 A | 9/1989 | Byrnes et al. |
| 5,070,025 A | 12/1991 | Klein et al. |
| 5,171,662 A | 12/1992 | Sharma |
| 5,436,131 A | 7/1995 | Condra et al. |
| 5,986,094 A | 11/1999 | Ghoshal et al. |
| 6,335,429 B1 | 1/2002 | Cai et al. |

FOREIGN PATENT DOCUMENTS

| DE | 38 19 846 A1 | 12/1989 |
| EP | 0 745 602 A2 | 4/1996 |
| EP | 1 207 394 A2 | 5/2002 |
| FR | 2 773 994 | 1/1998 |
| WO | WO 91/16336 | 10/1991 |
| WO | WO 91/19000 | 12/1991 |
| WO | WO 94/23041 | 10/1994 |
| WO | WO 95/32002 | 11/1995 |
| WO | WO 97/43438 | 11/1997 |
| WO | WO 98/53093 | 11/1998 |
| WO | WO 99/18856 | 4/1999 |
| WO | WO 99/67417 | 12/1999 |
| WO | WO 00/04914 | 2/2000 |

OTHER PUBLICATIONS

Gan, Z. et al., "Biotinylated enzyme inhibitorsorbent assay: a specific method for quantifying enzyme and its inhibitor" (1998), Anal. Biochem., 265:69–73.

Gan, Z. et al., "Rapid fluorometric method for the measurement of HIV protease inhibitor levels in patient serum", XIV International AIDS Conference, Jul. 7–12, 2002, published on the Internet of Jul. 8, 2002, 2 pages.

Novak, R.M. et al., "Functional measurement of HIV protease inhibitor levels in patient serum by a rapid fluorometric method", XIV International AIDS Conference, Jul. 7–12, 2002, published on the Internet on Jul. 8, 2002, 2 pages.

Wlodawer, A. et al. "Structure–based inhibitors of HIV–1 protease" (1993), Annu. Rev. Biochem., 62:543–85.

Akeb, F. et al, "Quantification of plasma and intracellular levels of the HIV protease inhibitor ritonavor by competitive ELISA" (2002), J. Immunol. Methods, 263:1–9.

(List continued on next page.)

Primary Examiner—Hankyel T. Park
(74) Attorney, Agent, or Firm—Marilyn L. Amick; Roche Diagnostics Operations, Inc.

(57) ABSTRACT

A method for quantifying an HIV protease inhibitor in a sample includes combining HIV protease, a conjugate comprising an HIV protease inhibitor analog, and a sample suspected of containing an HIV protease inhibitor. The HIV protease and the conjugate are capable of forming a detectable complex. The method also includes measuring the amount of the detectable complex, and relating the amount of the detectable complex to a concentration of the HIV protease inhibitor in the sample.

42 Claims, 3 Drawing Sheets

OTHER PUBLICATIONS

Barry, M. et al., "Protease inhibitors in patients with HIV disease: clinically important pharmacokinetic considerations" (1997), *Clin. Pharmacokinet.*, 32: 194–209.

Dandliker, W.B., et al., "Quantification of the antigen–antibody reaction by the polarization of fluorescence" *Bioche. Biophys. Res. Comm.* (1961) 5(4):299–304.

Chapman, J.G. et al., (2000), *J. Am. Chem. Soc.*, 122:8303–8304.

Fournot, S. et al., "Development and standardization of an immuno–quantified solid phase assay for HIV–1 aspartyl protease activity and its application to the evaluation of inhibitors" (1997), *Anal. Chem.*, 69:1746–1752.

Gan, Z., "Protease and protease inhibitor assays using biotinylated casein coated on a solid phase" (1999), *Anal. Biochem.*, 268(1):151–6.

Geoghegan, K.F. et al., "Fluorescence–based continuous assay for the aspartyl protease of human immunodeficiency virus–1" (1990), *FEBS*, 262(1): 119–122.

Graves, M.C. et al., "11–kDa form of human immunodeficiency virus protease expressed in *Escherichia coli* is sufficient for enzymatic activity" (1988), *Proc. Natl. Acad. Sci. USA*, 85: 2449–2453.

Konvalinka, J. et al., Configurations of diastereomeric hydroxyethylene isosteres strongly affect biological activities of a series of specific inhibitors of human.

Krafft, G.A. and Wang, G.T., "Synthetic approaches to continuous assays of retroviral protease" (1994), in Methods in Enzymology (Kuo, L.C. and Shafer, J.A., eds.), vol. 241, pp. 70.

Leibenguth, P. et al., "Therapeutic drug monitoring of HIV protease inhibitors using high–performance liquid chromatography with ultraviolet or photodiode array detection" (2001), *Therapeutic Drug Monitoring*, 23:679–688.

Markgren, P.–O. et al., "Screening compounds interacting with HIV–1 protease using optical biosensor technology" (1998), *Anal. Biochem.*, 265:340–350.

Markgren, P.–O. et al. "Kinetic analysis of the interaction between HIV–1 protease and inhibitors using optical biosensor technology" (2000), *Anal. Biochem.*, 279:71–78.

Martin, C.R. et al. (May 1, 1998), *Analytical Chemistry News and Features*, 322A–327A.

Marzonlini, C., et al., "Simultaneous determination of the HIV protease inhibitors indinavir, amprenavir, saquinavir, ritonavir and the non–nucleoside reverse transcriptase inhibitor efavirenz by high–performance liquid chromatography after solid–phase extraction" (2000), *J. Chromatogr.*, 740: 43–58.

Nashed, N.T. et al., "Continuous spectrophotometric assay for retroviral proteases of HIV–1 and AMV" (1989), *Biochem. Biophys. Res. Comm.*, 163: 1079–1085.

Navia, M.A. et al., "Three–dimensional structure of aspartyl protease from human immunodeficiency virus HIV–1" (1989), *Nature*, 337: 615–620.

Nutt, R.F. et al., "Chemical synthesis and enzymatic activity of a 99–residue peptide with a sequence proposed for the human immunodeficiency virus protease" (1988), *Proc. Natl. Acad. Sci. USA*, 85: 7129–7133.

Poirier, J.M. et al., "Simultaneous determination of the five HIV–protease inhibitors: amprenavir, indinavir, nelfinavir, ritonavir, and saquinavir in human plasma by solid–phase extraction and column liquid chromatography" (2000), *Ther. Drug Monit.*, 22: 465–473.

Rashkovetsky, L.G. et al., "Automated microanalysis using magnetic beads with commercial capillary electrophoretic instrumentation" (1997), *Journal of Chromatography A*, 781:197–204.

Remmel, r.P. et al., "Simultaneous HPLC assay for quantification of indinavir, nelfinavir, ritonavir, and saquinavir in human plasma" (2000), *Clin. Chem.*, 46 (1):73–81.

Rich, D.H. et al., "New hydroxyethylamine HIV protease inhibitors that suppress viral replication" (1992), *J. Med. Chem.*, 35: 3803–3812.

Richards, A.D. et al., "Sensitive, soluble chromogenic substrate for HIV–1 protease" (1990), *J. Biol. Chem.*, 265: 7733–7736.

Roberts, N.A. et al., "Rational design of peptide–based HIV protease inhibitors" (1990), *Science*, 248: 358–361.

Sham, H.L. et al., "Synthesis and antiviral activities of the major metabolites of the HIV Protease Inhibitor ABT–378 (Lopinavir)" (2001), *Bioorganic and Medicinal Chemistry Letters* 11, 1351–1353.

Singh, A. et al., "An enzyme immunoassay for detection of Japanese encephalitis virus induced chemotactic cytokine" (2000), *J. Biosci.*, 25(1): 47–55.

Tomaszek, T.A. et al., "Chromophoric peptide substrates for the spectrophotometric assay of HIV–1 protease" (1990), *Biochem. Biopys. Res. Comm.*, 168(1): 274–280.

Toth, M.V. and Marshall, G.R., "A simple, continuous fluorometric assay for HIV protease" (1990), *Int. J. Peptide Protein Res.*, 36: 544–550.

Wiltshire, H.R. et al., "Chromatographic and immunochemical approaches to the analysis of the HIV protease inhibitor saquinavir in plasma" (2000), *Analyt. Biochem.*, 281: 105–114.

Wlodawer, A. et al. "Conserved folding in retroviral protease: crystal structure of a synthetic HIV–1 protease" (1989), Science, 245: 616–621.

Mansfeld, HW, Schulz, S., Grutz, G., von Baehr, R., Ansorge, S. "Detection of inhibition of HIV–1 protease activity by an enzyme–linked immunosorbent assay (ELISA)". Journal of Immunological Methods, 161(1993) 151–155 (1993.

Sarubbi, E., Nolli, ML., Andronico, F., Stella, S., Saddler, G., Selva, E., Siccardi, A., Denaro, M. "A high throughput assay for inhibitors of HIV–1 protease". FEBS 09419, vol. 279, No. 2, 265–269.

John, L., Marra, F., Ensom, MHH. "Role of Therapeutic Drug Monitoring for Protease Inhibitors". The Annals of Pharmacotherapy, Jun. 2001, vol. 35, pp 745–754.

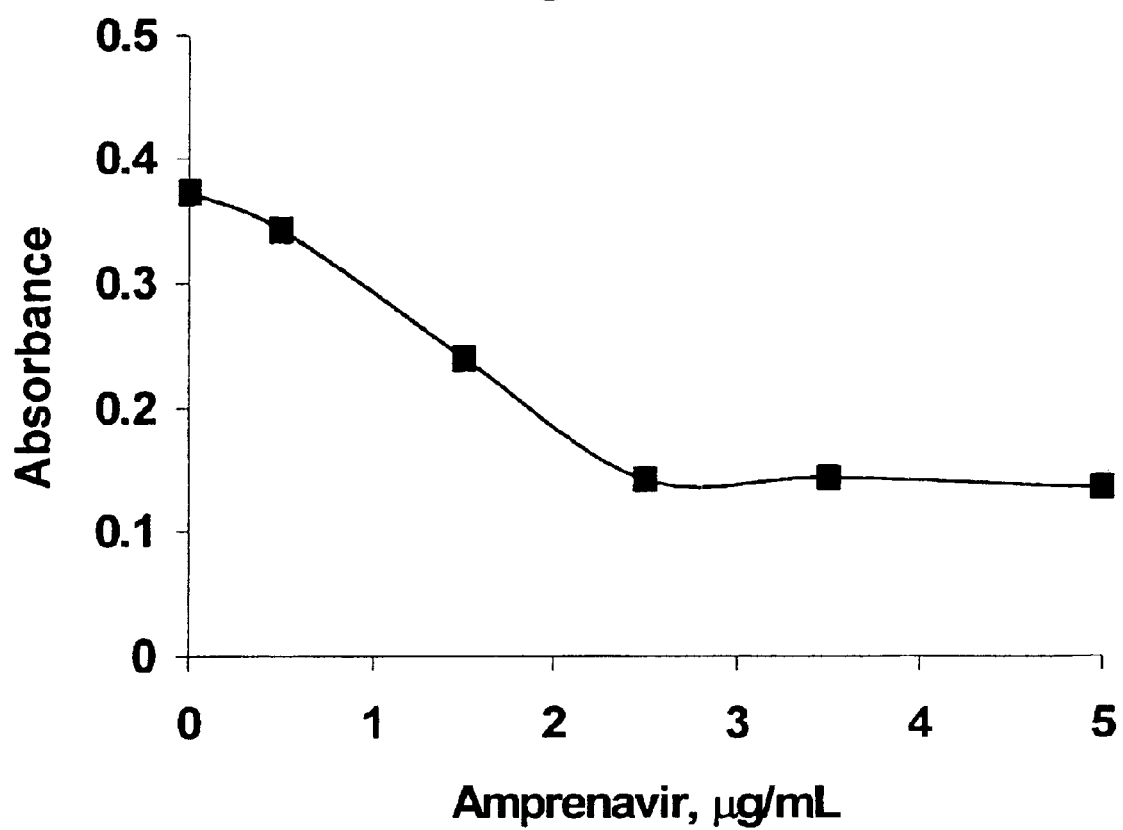

METHOD, ASSAY, AND KIT FOR QUANTIFYING HIV PROTEASE INHIBITORS

BACKGROUND

The clinical care of patients having acquired immunodeficiency disease syndrome (AIDS) has been substantially improved by the introduction of compounds which function as potent and specific HIV protease inhibitors. It is believed that the human immunodeficiency virus (HIV) is the causative agent responsible for AIDS, and that the enzyme HIV protease is responsible for catalyzing specific cleavages in the gag and gag-pol polypeptides of the HIV. A virus that synthesizes a mutationally inactivated HIV protease does not generally form infectious virions. HIV protease is thus an important target for which drugs against AIDS can be designed. HIV protease inhibitors can cause a reduction or cessation of the activity of HIV protease.

Currently, there are six HIV protease inhibitors approved by the Food and Drug Administration (FDA) for treatment of AIDS patients—amprenavir, indinavir, lopinavir, nelfinavir, ritonavir, and saquinavir. Combination therapies involving HIV protease inhibitors and HIV reverse transcriptase inhibitors are the cornerstones of currently recommended therapies for HIV infection. Not all AIDS patients show the same optimal response to a combination therapy regimen. There can be a large variability in drug response between individual patients. Relationships between systemic exposure to protease inhibitors and antiviral effect have been supported by accumulating clinical information. When a combination therapeutic regimen is administered to a patient, potential pharmacokinetic drug-drug interactions can improve or weaken the treatment. Patient compliance, which directly relates to maintenance of adequate drug levels, may also affect the outcome of the treatment.

It is thus desirable to measure concentrations of HIV protease inhibitors in patients to ensure that drug exposure is sufficient to maintain antiviral activity in AIDS patients. In addition, the quantitative measurement of HIV protease inhibitors in biological samples from test subjects is crucial in the drug development process. Other measurements of interest in the treatment of HIV include the measurement of the metabolites of HIV protease inhibitors, and the measurement of anti-HIV protease antibodies. The presence and amount of metabolites can provide information regarding the effectiveness of the therapeutic treatment. The presence of anti-HIV protease antibodies indicates infection of a patient by HIV, and the detection of the antibodies can therefore be used to diagnose possible infection.

Typically, HIV protease inhibitors in patient samples have been quantified by assay methods which require sophisticated and expensive instrumentation, making the analysis difficult to perform in a clinical setting. For example, plasma samples can be analyzed for the presence of numerous HIV protease inhibitor compounds simultaneously using chromatographic methods such as high-performance liquid chromatography (HPLC) or HPLC coupled with dual mass spectrometry (HPLC/MS/MS). See, for example, Poirier, J. M. et al., *Ther. Drug Monit.* 22:465–473 (2000); Marzonlini, C., et al., *J. Chromatogr.* 740:43–58 (2000); and Remmel, R. P. et al., *Clin. Chem.* 46(1):73–81 (2000). The plasma samples are typically subjected to solid-phase extraction procedures prior to examination. Thus, the plasma is not analyzed directly but must be modified, adding complexity and expense to the analysis.

Radioimmunoassays typically involve competitive interaction between a radiolabeled conjugate containing an HIV protease inhibitor analog and any free HIV protease inhibitor in the sample. The receptor is generally an antibody for the particular HIV protease inhibitor. In an example of a radioimmunoassay, an analog of an HIV protease inhibitor labeled with iodine-125 is reported to compete with any HIV inhibitor compound in a sample of patient plasma for binding with an antibody. The precipitated antibody complexes are then analyzed for their level of radioactivity to determine the concentration of the HIV protease inhibitor compound. See, for example, Wiltshire, H. R. et al. *Analyt. Biochem.* 281:105–114 (2000). In an example of an assay which indirectly uses a radioimmunoassay, HIV protease can be added to a sample together with a substrate for HIV protease. Cleavage of the substrate can then be measured by a radioimmunoassay utilizing an antibody which specifically binds the cleavage products. An absence of cleavage products indicates the presence of anti-HIV protease antibodies. See, for example, U.S. Pat. No. 5,171,662.

All of these methods for measuring inhibitors and/or their metabolites have met with mixed success. There is thus a need for an improved method to quantify HIV protease inhibitors and/or their metabolites in a biological sample. It is desirable that such a method can be easily and rapidly carried out on currently available analytical instrumentation in clinical settings.

SUMMARY

In one aspect of the invention, there is a method for quantifying an HIV protease inhibitor in a sample, comprising combining an HIV protease, a conjugate comprising an HIV protease inhibitor analog, and a sample suspected of containing an HIV protease inhibitor; wherein the HIV protease and the conjugate form a detectable complex; measuring the amount of the detectable complex, and relating the amount of said detectable complex to a concentration of the HIV protease inhibitor in the sample.

In another aspect of the invention, there is a method for quantifying an HIV protease inhibitor in a sample, comprising combining an HIV protease, a conjugate comprising a carrier and at least two HIV protease inhibitor analogs linked to the carrier, and a sample suspected of containing an HIV protease inhibitor; wherein the HIV protease is immobilized on a surface of a microparticle, the HIV protease and the conjugate together undergo agglutination; measuring the agglutination; and relating the amount of agglutination to a concentration of the HIV protease inhibitor in the sample.

In yet another aspect of the invention, there is a method for quantifying an HIV protease inhibitor in a sample, comprising combining a multivalent carrier comprising at least two HIV protease enzymes, a conjugate comprising a microparticle and an HIV protease inhibitor analog, and a sample suspected of containing an HIV protease inhibitor, wherein the HIV protease and the conjugate together undergo agglutination, and the sample is human serum or human plasma; measuring the agglutination; and relating the amount of agglutination to a concentration of the HIV protease inhibitor in the sample.

In yet another aspect of the invention, there is a method for quantifying an HIV protease inhibitor in a sample, comprising combining an HIV protease, a conjugate comprising a label and an HIV protease inhibitor analog linked to the label, and a sample suspected of containing an HIV protease inhibitor, wherein the HIV protease and the conjugate together form a detectable complex; measuring the amount of the detectable complex by monitoring a change in fluorescence polarization; and relating the amount of the detectable complex to a concentration of the HIV protease inhibitor in the sample.

In yet another aspect of the invention, there is a method for monitoring a concentration of an HIV protease inhibitor in an organism, comprising administering a dose of an HIV protease inhibitor to the organism; obtaining a fluid sample from the organism; combining the sample with an HIV protease and a conjugate comprising an HIV protease inhibitor analog, wherein the HIV protease and the conjugate together form a detectable complex; measuring the amount of the detectable complex in the sample; and relating the amount of the detectable complex to a concentration of the HIV protease inhibitor in the organism.

In yet another aspect of the invention, there is a reagent for quantifying an HIV protease inhibitor in a sample, comprising a particle comprising a surface, and HIV protease immobilized on the surface of the particle. The HIV protease forms a detectable complex with a conjugate, wherein the conjugate comprises an HIV protease inhibitor analog.

In yet another aspect of the invention, there is a kit for quantifying an HIV protease inhibitor in a sample, comprising HIV protease, and a conjugate comprising an HIV protease inhibitor analog.

BRIEF DESCRIPTION OF THE DRAWINGS

FIG. 3 is a graph of absorbance as a function of the concentration of amprenavir at various concentrations in normal human serum, using a competitive assay including the conjugate of FIG. 1.

DETAILED DESCRIPTION

Figure 1:
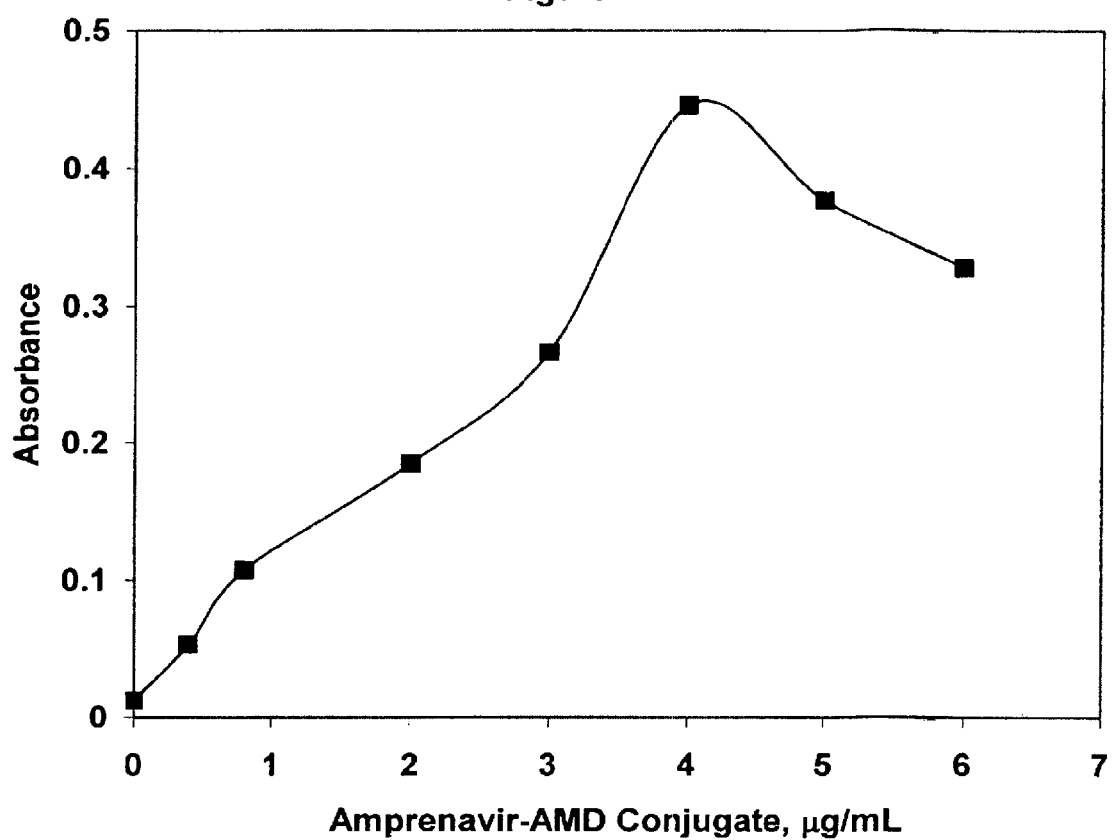
FIG. 1 is a graph of absorbance as a function of the concentration of an amprenavir/aminodextran conjugate containing an average of 3.75 amprenavir analog moieties per aminodextran.

The present invention relates to an assay system for determining the concentration of HIV protease inhibitors (HIV-PIs) in a sample. The system includes HIV protease (HIV-PR) enzyme, a conjugate, and a sample suspected of containing HIV-PIs. According to the invention, the conjugate and HIV-PIs present in the sample compete for the binding to the HIV-PR. Upon contacting of the HIV-PR by the conjugate and a sample containing HIV-PIs, the levels of HIV-PR bound to the conjugate change, and this change can be measured and correlated to the concentration of the HIV-PIs in the sample.

The term "HIV protease" (HIV-PR) means an enzyme responsible for posttranslational processing of the gag and gag-pol polypeptides of the HIV. Two types of HIV, which encode HIV-PR, are HIV-1 and HIV-2. HIV-1 is a highly variable virus which mutates very readily, resulting in many different strains of HIV-1. These strains can be classified according to groups (for example, M and O) and according to subtypes. Examples of HIV protease thus include HIV-1 PR and HIV-2 PR, as well as engineered HIV-PR.

The term "HIV protease inhibitor" (HIV-PI) includes HIV protease inhibitor compounds, active metabolites of HIV protease inhibitor compounds, and anti-HIV protease antibodies. Examples of HIV protease inhibitor compounds and metabolites thereof include peptides, organic compounds, organometallic compounds, and metallic complexes which can reduce or eliminate the activity of HIV protease. Specific examples of HIV protease inhibitor compounds include the compounds which are currently approved by the FDA for treatment of AIDS patients, namely amprenavir, indinavir, lopinavir, nelfinavir, ritonavir, and saquinavir. An anti-HIV protease antibody is an antibody which has a specific binding affinity for the HIV protease enzyme to the exclusion of other substances. The term "antibody" includes polyclonal antibodies, monoclonal antibodies and antibody fragments.

The term "analyte" means a substance, or group of substances, whose presence or amount in a sample is to be determined including, but not limited to, any drug or drug derivative, hormone, protein antigen or oligonucleotide. In the present assay system, the analyte is an HIV protease inhibitor, including an HIV protease inhibitor compound, a metabolite of an HIV protease inhibitor compound, or an anti-HIV protease antibody.

The term "receptor" means a specific binding partner of an analyte, and is meant to include any substance, or group of substances, which has a specific binding affinity for the analyte to the exclusion of other substances. Examples of receptors includes enzymes and antibodies. In the present assay system, HIV protease acts as a receptor for an HIV-PI and/or for a conjugate containing an HIV-PI analog.

The term "HIV-PI analog" means a substance, or group of substances, which behaves essentially the same as an HIV protease inhibitor with respect to binding affinity for HIV protease. An HIV-PI analog is typically an HIV-PI that has been modified or derivatized such that it will mimic the interaction of the HIV-PI with HIV-PR. An HIV-PI analog thus includes any modification of an HIV-PI. For example, an HIV-PI analog may be identical to the HIV-PI except for the presence of a linkage between the HIV-PI and another substance, such as an atom, a linking group, a label, or a carrier substance. Examples of HIV-PI analogs include, but are not limited to, analogs of HIV protease inhibitor compounds, analogs of metabolites of HIV protease inhibitor compounds, and analogs of anti-HIV protease antibodies.

The term "conjugate" means a composite of an HIV-PI analog linked to another substance, for example a carrier, a label or a solid phase, and is capable of specifically binding to a receptor. For example, a conjugate containing an HIV-PI analog may specifically bind with HIV-PR through the analog. A conjugate containing an HIV-PI analog can be prepared, for example as described in a co-pending application Ser. No. 10/192,052 filed on Jul. 7, 2002, which is incorporated herein by reference.

The term "label" means an identifying tag which, when attached to an HIV-PI analog as part of a conjugate, can be used to detect the binding of the conjugate with an appropriate receptor. A label may be attached to the HIV-PI analog directly or indirectly by means of a linking or bridging moiety. Examples of commonly used labels include fluorescent labels such as fluoresceins and rhodamines; luminescent compounds such as dioxetanes and luciferin; radioactive isotopes such as $^{125}$I; chemiluminescent labels such as acridinium esters; electrochemiluminescent labels such as ruthenium bipyridyl; enzymes such as peroxidase and beta-galactosidase; and enzyme substrate labels.

The term "carrier" means a substance, commonly a protein, which can join with one or more HIV-PI analogs, thereby enabling the detection of any binding of the HIV-PI analog with a receptor. Examples of carriers include proteins such as bovine serum albumin (BSA); synthetic or natural polysaccharides; and polymers such as aminodextran (AMD).

The term "detectable complex" means a complex formed by a receptor and a conjugate, the amount of which can be measured by monitoring a change in a signal from the complex and/or its surroundings. The change in signal may be, for example, the formation of a measurable precipitate; a change in a characteristic of a spectroscopic absorbance, emission, luminescence or fluorescence; or a change in electrical properties.

The term "peptide" means any compound formed by the linkage of two or more amino acids by amide (peptide) bonds, usually a polymer of α-amino acids in which the α-amino group of each amino acid residue (except the $NH_2$-terminal) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

The term "covalent bond" means a chemical bond between two species, and may involve single bonds or multiple bonds. In contrast, the term "non-covalent bond" means chemical or physical interactions that do not form chemical bonds. Non-covalent bonding thus includes hydrophobic/hydrophilic interactions, Hydrogen-bonding, van der Waals interactions, and ionic and metallic interactions. For example, adsorption of a substance to a surface is non-covalent, whereas coupling of a substance to a surface, such as through carbodiimide or N-hydroxy succinimide (NHS) coupling, is covalent.

The term "biological sample" means a bodily fluid obtained from a living organism. A biological sample is preferably an aqueous mixture, for example, urine, whole blood, plasma, serum, saliva, semen, stool, sputum, cerebral spinal fluid, tears, mucus or the like, but preferably is plasma or serum, and more preferably is human plasma or human serum. Any sample that is suspected of containing an HIV-PI can be analyzed by the method of the present invention. The sample can be pretreated if desired, including pretreatment by dilution, filtration, and/or centrifugation. The sample can be prepared in any convenient medium that does not interfere with the assay, and an aqueous medium is preferred.

The term "calibration material" means any standard or reference material containing a known amount of the analyte to be measured. The sample suspected of containing the analyte and the calibration material are assayed under conditions which are as identical as possible. Analyte concentration is then calculated by comparing the results obtained for the unknown sample with results obtained for the standard.

The term "solid phase" means a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component of an assay is distinguished from inert solid surfaces with which the assay may be in contact in that a "solid phase" contains at least one moiety on its surface which is intended to interact with one or more of the components of the assay mixture.

An assay system for determining the concentration of HIV protease inhibitors (HIV-PIs) in a sample can include HIV-PR and a conjugate containing an HIV-PI analog. The conjugate can bind to the HIV-PR to form a detectable complex; however any HIV-PIs present can also bind to the HIV-PR, thus competing with the conjugate. Upon contacting of the HIV-PR with the conjugate and a sample containing HIV-PIs, the levels of HIV-PR bound to the conjugate change, and this change can be measured and correlated to the concentration of the HIV-PIs in the sample.

In this assay format, the HIV protease enzyme acts as a receptor for the conjugate and for the HIV protease inhibitors in the sample. Typically, a conventional immunoassay uses an antibody that specifically binds the analyte and the analyte analog portion of a conjugate. See, for example, European Patent Application Publication EP 1 207 394 A2, which is incorporated herein by reference. This method can require the preparation of unique antibodies for each variety of HIV-PI to be analyzed. By using HIV-PR as a receptor, any type of HIV-PI may be quantified using a single assay system, since the HIV-PR will be inhibited by any HIV-PI in a sample. This format can provide for advantageous diagnostic assay characteristics. For example, a sample containing a variety of different HIV-PIs can be analyzed in a single assay, allowing a convenient quantification of overall HIV-PI levels in a sample. Also, a single type of conjugate can be used to analyze for a variety of HIV-PIs, further contributing to the simplicity of the assay.

The HIV-PR may be present in an assay mixture as a free enzyme, or it may be bound to another substance, such as to a surface of a solid phase or to a carrier. The use of HIV-PR as a receptor can be applied to both homogeneous assays and heterogeneous assays. In a heterogeneous assay, a solid phase component of the assay is separated from the rest of the liquid assay mixture before the measurement of interest is performed. In contrast, a homogeneous assay allows measurements to be obtained from the complete assay mixture, including the sample.

The use of a solid phase in a diagnostic assay can provide a convenient way of localizing and/or separating particular components of an assay mixture, so that the measurement of interest can be obtained. A wide variety of assay configurations are known which include the use of a solid phase component, and these may be classified roughly as either heterogeneous or homogeneous. Solid phase components in either homogeneous or heterogeneous formats may contain HIV-PR as an active moiety on the solid phase surface. Thus, the HIV-PR can act as a receptor capable of binding both HIV-PIs and detectable conjugates.

The surface of a given solid phase component can be modified to include HIV-PR by a variety of methods. For example, HIV-PR can be adsorbed onto a surface by contacting the surface with a liquid mixture containing the HIV-PR enzyme. In another example, an antibody which binds HIV-PR without obscuring critical binding sites of the enzyme can be adsorbed or bound to the surface, and the HIV-PR subsequently can be immobilized on the surface through its interaction with the antibody. In yet another example, biotin, avidin, or streptavidin can be used to immobilize a modified HIV-PR which contains the appropriate binding partner. In this example, it may be convenient to modify the HIV-PR with the smaller biotin moiety and to modify the solid surface with avidin or streptavidin. In yet another example, HIV-PR may be immobilized by covalent attachment such as carbodiimide coupling, N-hydroxy succinimide (NHS) ester coupling, or other chemical coupling techniques. See, for example, Markgren, P.-O. et al. *Analytical Biochemistry* 265, 340–350 (1998), which is incorporated herein by reference.

Solid phase components for heterogeneous assays may be stationary components, such as a tube, strip, cuvette or microtiter plate, or may be non-stationary components, such as beads and microparticles. Microparticles can also be used as a solid phase for homogeneous assay formats. A variety of microparticles that allow either non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example C. R. Martin et al. *Analytical Chemistry—News & Features*, May 1, 1998, 322A–327A, which is incorporated herein by reference.

For example, useful microparticle reagents may be formed by adsorption of the HIV-PR onto the surface of the microparticles. Preferred microparticles include polystyrene-based latex microparticles having diameters between 0.1 and 1.0 micrometers ($\mu$m). The surface of the microparticles can include carboxylate groups (—COO— and —COOH). Carboxylate groups can be introduced to surfaces, for example by hydrolysis reactions, by treatment with a carboxylating reagent, or by formation of self-assembled monolayers (SAMs) containing carboxylate groups. See for example J. G. Chapman et al. *J. Am. Chem. Soc.*, 122, 8303–8304 (2000), which is incorporated herein by reference. For example, the microparticles may contain carboxylate groups in a concentration which provides a 5–200 $\text{Å}^2$, or preferably 10–120 $\text{Å}^2$ carboxylate surface parking area, which is defined as the surface area of the microparticle, divided by the total number of carboxylate groups on the surface.

In an example of immobilization of HIV-PR, the enzyme is adsorbed onto carboxylate-modified latex microparticles. The microparticles containing bound HIV-PR are then separated from the adsorption mixture and subjected to repeated cycles of washing and centrifugation. These modified particles may be stored at reduced temperature, for example at 4° C. for up to 2 weeks. The aqueous mixtures used for adsorption, washing, or preparing stock mixtures are buffered, preferably at a pH between 3.5 and 6.5. If a more robust, engineered HIV-PR is used, the handling and storage conditions may be more flexible.

A solid phase material, whether stationary or non-stationary, having HIV-PR bound to its surface may be used in a competitive assay to quantify HIV-PIs in a sample. In such a competitive assay format, HIV-PIs in the sample compete with a conjugate for binding with the immobilized HIV-PR, which functions as a receptor. The binding of HIV-PR with the conjugate results in the formation of a detectable complex. Measurement of the amount of binding of the enzyme with the conjugate alone, compared with the amount of binding in the presence of HIV-PIs, can be correlated to the amount of the HIV-PIs in the sample that are competing with the conjugate.

One example of a homogeneous assay utilizing free HIV-PR enzyme as a receptor is fluorescence polarization. In fluorescence polarization assays, the conjugate includes a fluorescent tracer linked to the HIV-PI analog. This fluorescent conjugate competes with HIV-PI in a sample for binding to the HIV-PR. A conjugate which is bound to the HIV-PR will exhibit a fluorescence polarization which is different from that exhibited by an unbound conjugate. Thus, the detectable complex is quantified or measured by monitoring the change in fluorescence polarization of the assay mixture. The change in fluorescence polarization signal due to the presence of HIV-PIs can be correlated to the amount of HIV-PI in a sample. See for example *Biochem. Biophys. Res. Comm.* 5:299, 1961, which is incorporated herein by reference.

In general, fluorescence polarization techniques are based on the principle that a fluorescein labeled compound, when excited by linearly polarized light, will emit fluorescence having a degree of polarization inversely related to its rate of rotation. Several fluorescein derivatives from which fluorescein labeled tracers can be prepared are known and are commercially available. The majority of fluorescein derivatives are derived from the 5 or 6 position of fluorescein (also referred to as isomer I for the 5 position and isomer II for the 6 position) and include 5 or 6-N-hydroxysuccinimidylcarboxyfluorescein, 5-aminomethylfluorescein and 5-or 6-dichloro-1,3,5-triazin-2-ylaminofluorescein (DTAF). The signal of fluorescence polarization immunoassays can be quantified in terms of millipolarization units (mP), from which a calibration curve can be determined. The polarization of fluorescence decreases in a regular manner as the concentration of the analyte increases, and the concentration of analyte in the sample can be determined by comparison to the standard calibration curve. Fluorescence polarization assays, including procedures, instrumentation, and reagents, are described in U.S. Pat. Nos. 5,986,094; 5,070,025; 4, 868,132; and in European Patent Application No. EP 0 745 602 A1, which are all incorporated herein by reference.

In fluorescence polarization assays of HIV-PIs, fluorescence polarization is a function of the analyte concentration, and thus is suitable for quantifying HIV protease inhibitor compounds, metabolites of HIV protease inhibitor compounds, and anti-HIV protease antibodies. When the conjugate and HIV-PR are mixed together in the absence of free HIV-PI, most of the conjugate binds to the HIV-PR. As a result, when the bound tracer is excited with polarized light at an absorption wavelength, the light emitted at the emission wavelength remains highly polarized. However, if HIV-PIs are present in the sample, the HIV-PIs will compete with the conjugate for binding to the HIV-PR bound to the particles. Thus, more of the tracer will remain unbound, and the emitted light is less polarized. In one example of a fluorescence polarization assay for HIV-PIs, the conjugate includes an HIV-PI analog linked to fluorescein. The detection of the complex of the HIV-PR and the conjugate includes irradiating the sample with light at 489 nm, and measuring polarization of the light emitted at 520 nm.

One example of a homogeneous assay in which the HIV-PR receptor is bound to as surface of a solid phase is microparticle agglutination. In microparticle agglutination assays, the conjugate includes a plurality of HIV-PI analogs linked to a carrier substance. This multivalent conjugate competes with any HIV-PI in a sample for binding to a limited amount of HIV-PR bound to microparticles. As few as two, either of the same or of a different origin HIV-PI analogs linked to a carrier can be used, but an increased amount of HIV-PI analogs can also be linked to the carrier. The HIV-PI analogs that originate from different HIV-PIs must be competitors to the HIV-PIs in the sample. The multivalent nature of the conjugate results in crosslinking, and thus agglutination, of the microparticles when the conjugate binds to the immobilized HIV-PR. The amount of microparticle agglutination which occurs in the absence of HIV-PIs is thus reduced by the presence of any HIV-PI in the sample. The detectable complex can thus be measured or quantified by a variety of agglutinometric techniques including, for example, turbidity, nephelometry, angular anisotropy, and quasielastic light scattering. For example, turbidity measurements, which can be performed on a simple spectrophotometer, detect changes in absorbance due to the changes in microparticle size related to the degree of agglutination. See, for example, U.S. Pat. No. 4,480,042, and European Patent Application Publication EP 1 207 394 A2, both of which are incorporated herein by reference.

Microparticle agglutination assays may also be performed using an HIV-PI analog linked to a microparticle surface, in combination with a carrier linked to a plurality of HIV-PR enzymes. The conjugate in this assay contains the HIV-PI analog bound to the microparticle, and this conjugate competes with any HIV-PI in the sample for binding to the HIV-PR enzyme on the multivalent carrier. The detectable complex can be measured by agglutination techniques as described above. HIV-PI analogs can be linked to solid phase surfaces, for example, through covalent coupling and through adsorption of an HIV-PI analog linked to a carrier such as bovine serum albumin. Carriers linked to HIV-PIs, and the adsorption of such carriers to solid phase surfaces to form conjugates, are described, for example, in co-pending application Ser. No. 09/712,525 filed on Nov. 14, 2000, which is incorporated herein by reference.

For a homogeneous assay of HIV-PIs using microparticle agglutination, it may be useful to use an aqueous buffer having a pH between 3.5 and 6.5, or preferably between 4.5 and 5.5. Useful buffers may include sodium chloride at a concentration between 0.1 molar (M) and 1 M, or between 0.2 M and 0.8 M, and may also include an agglutination accelerator. Agglutination accelerators include, for example, poly(acrylic acid) (PAA), polyvinylpyrrolidone (PVP), and sodium dextransulfate, and may be present at a concentration between 0.5% and 3%, or preferably between 0.8% and 2.5%.

Heterogeneous assays can also be used to quantify HIV-PIs. Preferred heterogenous formats include enzyme linked solid phase receptor assays, in which the conjugate includes an HIV-PI analog linked to an enzyme. Enzyme linked solid phase receptor assays can be performed in competitive or non-competitive formats. In a competitive format, the enzyme-linked inhibitor analog competes with any analyte in a sample for binding to a limited amount of receptor that is immobilized on a solid phase. A variety of techniques may then be used for the detection of an enzyme label. Typically, the enzyme is responsible for the conversion of a substrate to a product that can be readily detected, either by its color or through another spectroscopic property such as fluorescence or luminescence. In one example, alkaline phosphatase may be used as an enzyme label, and nicotinamide adenine dinucleotide phosphate (NADPH) may be used as a detectable substrate.

In one example of an enzyme linked solid phase receptor assay for HIV-PIs, the solid phase may be microparticles. A sample suspected of containing HIV-PIs is incubated with a conjugate and microparticles containing immobilized HIV-PR. The amount of binding between the conjugate and the bound HIV-PR which occurs in the absence of HIV-PIs is reduced as result of the presence of any competing HIV-PIs in the sample. The unbound components of the sample and conjugate are then removed, for example by centrifugation and decantation. The microparticles can also be captured by a filter containing a glass-fiber matrix or a selective membrane. Furthermore, ferromagnetic particles can be separated by the application of a magnetic field, drawing the particles to the side or the base of the tube. The supernatant solution can be removed by aspiration or decantation. The microparticles isolated from the assay mixture can then be treated with a substrate for the linked enzyme label, and the amount of enzyme bound to the particles can be measured and related to the concentration of HIV-PIs in the original sample.

In another example of an enzyme linked solid phase receptor assay for HIV-PIs, the solid phase may be a stationary phase, such as a microtiter plate. The solid phase materials can be glasses, metals, polymers, plastics, papers, or membranes. Preferred materials are plastics such as polystyrene. In this example, a sample suspected of containing HIV-PIs is incubated with a conjugate in the presence of HIV-PR immobilized on a microtiter plate. The amount of HIV-PR binding which occurs in the absence of HIV-PIs is reduced as result of competing HIV-PIs in the sample. The unbound portion of the sample, including any unbound conjugate, is then removed by aspiration, followed with several washes and their subsequent aspirations. The microtiter plate can then be treated with a substrate for the linked enzyme label, and the amount of enzyme bound to the plate can be measured and related to the concentration of HIV-PIs in the original sample.

In yet another example of a heterogeneous assay for quantifying HIV-PIs, the HIV-PR may function as a receptor without being immobilized on a solid phase surface. For example, a conjugate which is capable of being immobilized either directly (via covalent coupling or adhesive binding) or indirectly (for example by avidin/biotin complexation), can compete with any free HIV-PI in a sample for binding to the free HIV-PR in an assay mixture. This assay mixture is then combined with a solid surface to which the conjugate can be directly or indirectly immobilized. Thus, any HIV-PR bound to the conjugate will be immobilized on the solid surface and can be separated from the rest of the assay mixture.

In an example of this type of heterogeneous assay, an HIV-PI analog linked to biotin can compete with any free HIV-PI in a sample for binding to free HIV-PR in an assay mixture. Microparticles containing avidin or streptavidin bound to the surface can be combined with this assay mixture, allowing the complexation of the biotin with the bound avidin or streptavidin. Thus, any HIV-PR bound to the analog will be immobilized on the microparticles. Similarly, a stationary solid phase having avidin or streptavidin bound to the surface can be combined with the assay mixture, allowing HIV-PR to be immobilized through the biotin complexation with the avidin or streptavidin. The components of the sample that are not bound to the solid phase, including any HIV-PR which has been competitively inhibited by free HIV-PI, are then removed using standard heterogeneous assay techniques. If the HIV-PI analog is linked to a label, the isolated solid phase can be analyzed using spectroscopic techniques. If the HIV-PI analog is not linked to a label, the isolated solid phase can be contacted with a labeled anti-HIV protease antibody to provide for spectroscopic analysis. The free HIV-PR can also be modified prior to the assay, for example to include a spectroscopic label or an electrochemiluminescent label. For example, HIV-PR linked to a ruthenium bypridyl moiety can be bound to an electrode surface containing streptavidin through its interaction with a conjugate containing biotin and an HIV-PI analog. The electrode can then be separated, treated with tripropylamine, and used for electrochemiluminescent analysis.

Preferably, both homogeneous and heterogeneous assays for HIV-PIs can be performed on commercial, automated spectroscopic analyzers to provide for expeditious clinical analysis. Examples of currently available automated spectroscopic analyzers include the COBAS/HITACHI and the COBAS INTEGRA (ROCHE DIAGNOSTICS SYSTEMS, Indianapolis). Once a spectroscopic analyzer has been calibrated for one or more HIV-PIs of interest, a sample having an unknown concentration of one or more of the HIV-PIs can be analyzed, and the resulting spectroscopic signal correlated with the concentration of the HIV-PI(s) in the sample. Examples of spectroscopic analyzers include UV-visible spectrophotometers, fluorometers, luminometers, and NMR instruments. Preferably, the measured concentration of HIV-PI(s) in the sample has a value between the lowest and highest concentrations used for the calibration.

The method of the present invention can be used to quantify HIV-PIs in biological samples. Biological samples include fluid samples from an organism, for example, urine, whole blood, plasma, serum, saliva, semen, stool, sputum, cerebral spinal fluid, tears, mucus or the like. Such fluids typically include a variety of components in addition to the water and the HIV-PI of interest, including various peptides, lipids, salts, and other compounds and/or antibodies. These extraneous components can interfere with the interaction between HIV-PR and either or both of the conjugate and the HIV-PI. For example, the conjugate and/or the HIV-PI may adsorb to or react with one or more of the extraneous components. The HIV-PR may also be nonspecifically inhibited by other peptides in the fluid. It is surprising and unexpected that, given the possibility of interference in assays of body fluids, HIV-PIs can be quantified in biological samples by the use of HIV-PR as a receptor.

The method of the present invention may thus be used to monitor the levels of HIV protease inhibitor compounds in patients to whom therapeutic doses have been administered. Evaluation of the levels of HIV protease inhibitor compounds and correlation to positive or negative symptoms can be used to modify the treatment of AIDS patients. The measurements of HIV protease inhibitor compounds may also be used to evaluate the effectiveness of such compounds or of combinations of such compounds. The method of the present invention may also be used to monitor the levels of anti-HIV protease antibodies in patients. Determinations of the presence of the antibodies can be helpful in diagnosing infection by HIV, and determinations of the levels of the antibodies can be helpful in evaluating a patient's response to the virus or to antiviral therapies.

The use of the method of the present invention may be facilitated by providing a test kit for measuring the concentration of HIV-PIs. For example, a test kit may contain, in packaged combination, microparticles containing HIV-PR bound to the surface, and a conjugate for the HIV-PR. In another example, a test kit may contain, in packaged combination, a stationary solid phase, such as a microtiter plate or cuvette, containing HIV-PR bound to the solid surface, and a conjugate for the HIV-PR. Preferably the solid phase containing the bound HIV-PR is packaged separately from the conjugate, especially for competitive assay formats. The conjugate component of the kit may be in liquid or in lyophilized form. Preferably the ingredients are provided in amounts such that the ratio of the reagents provides for substantial optimization of the method and assay. The kit may also contain one or more calibrators comprising a known amount of an HIV-PI. The kit may also contain instructions for carrying out the method of the present invention. For example, the kit may contain instructions to combine the bound HIV-PR and the conjugate with a biological sample and to measure the detectable signal from the assay mixture. The instructions may also provide the appropriate formulas to allow for convenient calculation of the concentration of HIV-PIs in the sample.

The test kit may be optimized for particular purposes. For example, the amount of immobilized HIV-PR and the type and amount of the conjugate may be varied to provide optimal sensitivity to anti-HIV protease antibodies for the diagnosis of HIV infection. In another example, the amount of bound HIV-PR and the type and amount of conjugate may be varied to provide optimal sensitivity to one particular HIV protease inhibitor compound. In yet another example, the amount of bound HIV-PR and the type and amount of conjugate may be varied to provide optimal sensitivity to a combination of HIV protease inhibitor compounds, such that the individual concentrations of the compounds can be measured. In yet another example, the amount of bound HIV-PR and the type and amount of conjugate may be varied to provide optimal sensitivity to metabolites of HIV protease compounds.

EXAMPLES

The following examples are provided by way of illustration and should not be seen as limiting the scope of the present invention.

Materials

The enzyme HIV-1 protease (0.65 milligrams per milliliter (mg/mL), 16 International Units per milligram (IU/mg)) was obtained from BACHEM AMERICAS (King of Prussia, Pa.).

Example 1

Conjugate Synthesis

An HIV-PI conjugate containing an amprenavir analog was prepared as described in a co-pending patent application Ser. No. 10/192,052 filed on Jul. 10, 2002, which is incorporated herein by reference.

1. Synthesis of N-(succinimido-oxycarbonyl-butyryl)-amprenavir

Amprenavir (0.1517 g) and succinimido-oxycarbonyl butyryl chloride (0.0817 g) were stirred overnight in anhydrous dimethylformamide (DMF) (3 mL) at 50° C. The mixture was evaporated to dryness under reduced pressure and directly purified by silica gel chromatography (15% tetrahydrofuran (THF) in ethyl acetate elution) to yield N-(succinimido-oxycarbonyl-butyryl)-amprenavir as a white solid (0.1395 g, 61%). Mass spectrometry: M+Na 739.2. Spectral data ($^1$H-NMR) was compatible with functionalization at the aniline nitrogen.

2. Synthesis of N-(succinimidyl-oxycarbonyl-propylamino-$^{co}$glycyl-glycyl-glutaryl)-amprenavir (a) N-(succinimido-oxycarbonyl-butyryl)-amprenavir (131.5 mg) and glycyl-glycyl-4-aminobutyric acid (43.4 mg, Bachem California Inc., Calif.) were stirred 7 hours in 25% aqueous borate (pH 10) in THF (5 mL). The mixture was evaporated to dryness under reduced pressure and directly purified by preparative reversed phase-HPLC (45% acetonitrile-water containing 0.1% trifluoroacetic acid) to yield N-(3-carboxypropylamino-$^{co}$glycyl-glycyl-glutaryl)-amprenavir as a white solid (98.2 mg, 65%). Mass spectrometry: M+H 817.4.

(b) N-(3-carboxypropylamino-$^{co}$glycyl-glycyl-glutaryl)-amprenavir (40.9 mg), N-hydroxysuccinimide (11.5 mg), and ethyl dimethylaminopropyl carbodiimide (19.2 mg) were, stirred 5 hours in 20% anhydrous DMF in methylene chloride (2.5 mL). The mixture was evaporated to dryness under reduced pressure and directly purified by silica gel chromatography (12% methanol in chloroform elution) to yield N-(succinimidyl-oxycarbonyl-propylamino-$^{co}$-glycyl-glycyl-glutaryl)-amprenavir as a white foam (37.9 mg, 83%). Mass spectrometry, M+H 938.4.

Example 2
Preparation of Amprenavir Reagents
1. Conjugate Preparation

The APV derivative used in conjugate preparation was N-(succinimidyl-oxycarbonyl-propylamino-co-glycyl-glycyl-glutaryl)-amprenavir, having the following structure:

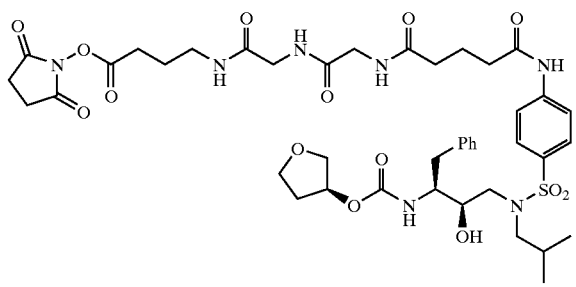

A stock solution of a carrier aminodextran (AMD; MW 40 kDa, 5.7 amines per molecule) was prepared by dissolving 80 mg of AMD in 4 mL of dimethyl sulfoxide (DMSO), for a final concentration of 20 mg/mL. A stock solution of 20 mg/mL of the APV derivative was prepared by dissolving 22 mg of APV derivative in 1.1 mL of DMSO. Lyophilized product was prepared by adding 0.183 mL of APV derivative stock solution (4:1 molar ratio of APV derivative to AMD) or 0.366 mL of APV derivative stock solution (8:1 molar ratio of APV derivative to AMD) dropwise with stirring to 2 mL of AMD stock solution at room temperature. The reaction mixture was then allowed to stir for 24 hours at room temperature. The reaction solution was next dialyzed against 80%, 60%, 40%, 20% DMSO and deionized water. The dialyzed solution was lyophilized and then kept in −20° C.

A stock solution of 0.5 mg/mL conjugate was prepared by dissolving 2 mg of lyophilized product in 4 mL of 20 mM Phosphate-Buffered Saline (PBS), pH 7.2. Serial dilutions, differing by factor of two, were made in the same buffer for a final volume of 2 mL, resulting in the conjugate solutions with concentrations of 0.25 mg/mL and 0.125 mg/mL. The same concentration stock solution and serial dilutions were made for AMD. The absorbance measurements at 264 nm were obtained for the various concentrations of the conjugate using AMD solution at corresponding concentrations as calibration blanks. The data and calculation results of load and average load are shown in Table 1.

TABLE 1

APV-AMD Conjugate with Two Different Load Ratios

| Load Ratio | APV-AMD µg/mL | Average Absorbance | APV, mM | Load | Average Load |
|---|---|---|---|---|---|
| 4:1 | 125 | 0.1643 | 6.5720E−03 | 2.10 | 2.15 |
| | 250 | 0.3327 | 1.3308E−02 | 2.13 | |
| | 500 | 0.6909 | 2.7636E−02 | 2.21 | |
| 8:1 | 125 | 0.2809 | 1.1236E−02 | 3.60 | 3.75 |
| | 250 | 0.5849 | 2.3394E−02 | 3.74 | |
| | 500 | 1.2188 | 4.8753E−02 | 3.90 | |

2. Microparticle Reagent Preparation
A) Pre-wash of Latex Microparticles 5 mL of 10% solid carboxylate-modified latex microparticle suspension (0.198 µm, 41 square angstrom parking area, made by SERADYN, INC. (Indianapolis, Ind.) was diluted to 1% solid with deionized water. The suspension was centrifuged at 32,600×g for 1 hr at 4° C. The pellet was saved and resuspended by sonication in deionized water. The suspension was centrifuged at 32,600×g for 1 hr at 4° C. The pellet was saved and resuspended by sonication in 50 mM 2-(N-Morpholino)-ethanesulfonic acid (MES), pH 5.5. The latex microparticles were stored at 4° C.

B) Adsorption of HIV-PR Onto Latex Microparticles 0.33 mL of 50 mM MES, pH 5.5, and 0.33 mL of pre-washed 1.18% solid latex suspension were added with stirring to a 1.7-mL microcentrifuge tube followed by addition of 0.33 mL of 0.3 mg/mL HIV-1 PR (provided in 0.1 M sodium acetate buffer, pH 5.5, 10% (v/v) glycerol, and 5% (v/v) ethylene glycol). The reaction solution was mixed well and incubated overnight at 4° C. Next day, the mixture was centrifuged at 32,600×g for 1 hr at 4° C. The pellet was saved and resuspended by sonication in 0.5 mL of 50 mM MES, pH 5.5. 0.5 mL of 2% Bovine Serum Albumin (BSA) (freshly dissolved in 50 mM MES, pH 5.5, 0.09% NaN$_3$) was added to the resuspended solution. The solution was well mixed and incubated overnight at 4° C. The next day, the mixture was centrifuged at 32,600×g for 1 hr at 4° C. The pellet was saved and resuspended by sonication in 1 mL of HIV-PR assay buffer (50 mM sodium acetate (NaOAc), pH 4.9, 200 mM sodium chloride (NaCl), 5 mM diothiothreitol (DTT), 10% (v/v) glycerol). Next, the mixture was centrifuged at 32,600×g for 1 hr at 4° C. The pellet was saved and washed with HIV-PR assay buffer as described above. After the final wash, the pellet was resuspended in 1 mL of HIV-PR assay buffer. Lastly, the final concentration of latex microparticles was determined by comparison of latex microparticles to the standard curves at five different wavelengths (340, 405, 500, 550 and 600 nm) on ROCHE COBAS MIRA (ROCHE DIAGNOSTICS, Indianapolis, Ind.).

Example 3
Analysis of Conjugate Binding

Figure 2:
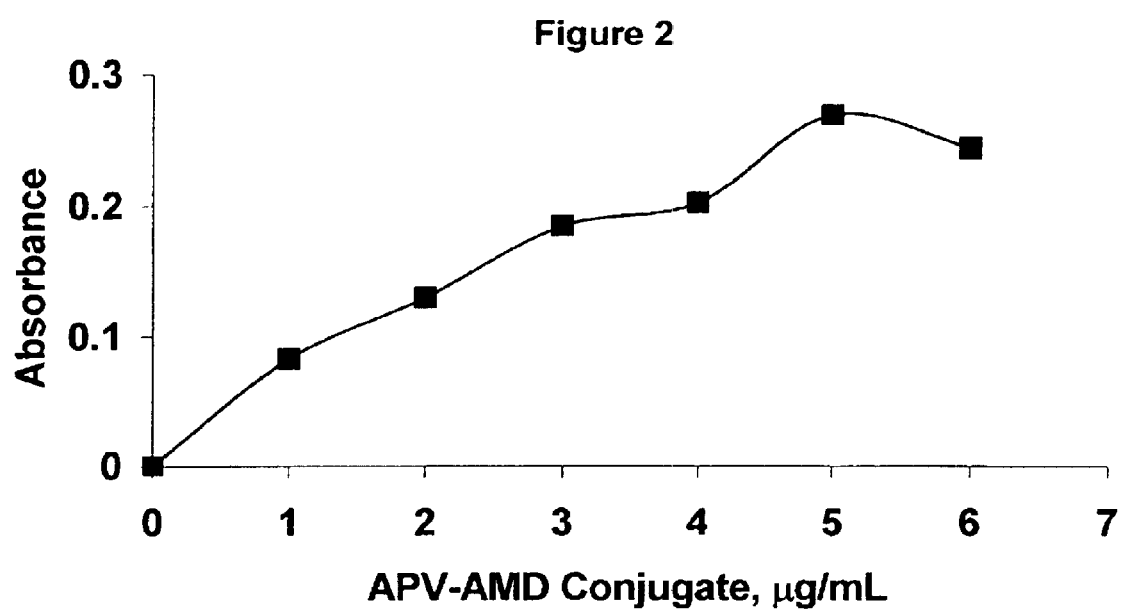
FIG. 2 is a graph of absorbance as a function of the concentration of an amprenavir/aminodextran conjugate containing an average of 2.15 amprenavir analog moieties per aminodextran.

Latex microparticle reagents prepared as described above were diluted with HIV-PR assay buffer for a 0.08% solid latex suspension. The 2.15:1 and the 3.75:1 APV-AMD conjugates at nine different concentrations (0, 0.4, 0.8, 1, 2, 3, 4, 5, 6 µg/mL) were each mixed with HIV-PR assay buffer and 2.5% polyacrylic acid (PAA). ROCHE ZERO CALIBRATOR (ROCHE DIAGNOSTICS, Indianapolis, Ind.) (normal human serum) was used as a serum sample. FIGS. 1 and 2 are graphs of the results obtained for the 3.75:1 and the 2.15:1 conjugates, respectively. These agglutination tests were run on ROCHE COBAS MIRA. The assay parameters on ROCHE COBAS MIRA are shown in Table 2.

TABLE 2

Assay Parameters for ROCHE COBAS MIRA

| Wavelength | 600 nm |
|---|---|
| Temperature | 37° C. |
| Sample Volume | 2 Ml |
| Conjugate Reagent | 100 µL |
| Microparticle Reagent | 95 µL |
| Water Push | 0 |
| Sample/Conjugate Preincubation | 2.08 min |
| Reading Time | 6.25 min |

Example 4
Preparation of Calibration Curve for Amprenavir

A stock solution of 1 mg/mL of APV was prepared by dissolving 1 mg APV in 1 mL of DMSO. The APV stock was spiked into ROCHE ZERO CALIBRATOR to obtain a series of the serum samples at concentrations of 0.5, 1.5, 2.5, 3.5 and 5 µg/mL. The microparticle reagent was prepared as described in Example 1. The conjugate reagent contained 5 µg/mL conjugate APV:AMD (3.75:1) in HIV-PR assay buffer and 2.5% PAA. The agglutination inhibition/replacement tests were run on ROCHE COBAS MIRA using various concentrations of APV prepared in normal human serum. The assay parameters for ROCHE COBAS MIRA used are the same as in Example 2. The results of the competitive inhibition assay as measured by microparticle agglutination at various concentrations of APV are illustrated in FIG. 3.

Example 5
Determination of HIV-PI Levels In Control Subjects

Stock solutions containing a conjugate and HIV-PR bound to microparticles are prepared as in Example 1. A stock solution containing protease inhibitors (indinavir sulfate, nelfinavir mesylate, ritonavir, and saquinavir) is prepared in methanol as described in Remmel et al. Different calibration solutions are prepared by dilution from the stock solution such that the final concentration ranges are 0.05–19.4 µg/ml for indinavir, 0.02–8.6 µg/ml for nelfinavir, 0.05–20.0 µg/ml for ritonavir, and 0.02–8.8 µg/ml for saquinavir (Remmel et al.). A quality control stock solution was prepared separately in methanol. Serum or plasma samples are obtained from the healthy human volunteers and are then supplemented with a portion of the stocksolution of the HIV protease inhibitors. These samples supplemented with HIV-PIs are then incubated with the microparticle solution with HIV-PR and the conjugate. The concentration of the protease inhibitors is established by monitoring the microparticle agglutination of HIV-PIs in the serum or plasma samples. The increased absorbance, due to the increasing microparticle size from agglutination, is measured by a spectrophotometer.

Since the concentration of HIV protease inhibitors is inversely proportional to the decrease in the measured absorbance, the concentration of protease inhibitors in the serum or plasma is calculated.

Example 6
Determination of HIV-PI Levels In AIDS Patients

Stock solutions containing a conjugate and HIV PR bound to microparticles are prepared as in Example 1. Serum or plasma samples are obtained from AIDS patients 8 hours after treatment with an oral dose of protease inhibitors (HIV-PI). The serum or plasma samples from AIDS patients are then incubated with the microparticle solution with HIV-PR and the conjugate, and the concentration of HIV-PIs is established by measuring the microparticle agglutination of HIV-PIs in the serum or plasma samples. The increased absorbance, due to the increasing microparticle size from agglutination, is measured by a spectrophotometer.

Since the concentration of HIV protease inhibitors is inversely proportional to the decrease in the measured absorbance, the concentration of protease inhibitors in the serum or plasma is calculated.

Example 7
Determination of Anti-HIV Protease Antibody Levels In Biological Samples Stock solutions containing a conjugate and HIV PR bound to microparticles are prepared as in Example 1. Serum or plasma samples are obtained from AIDS patients within the first year from the AIDS diagnosis, and are then are then incubated with the microparticle solution with HIV PR and the conjugate, and the concentration of HIV-PIs is established by measuring the microparticle agglutination of HIV-PIs in the serum or plasma samples. The increased absorbance, due to the increasing microparticle size from agglutination, is measured by a spectrophotometer.

Since the concentration of anti-HIV protease antibodies is inversely proportional to the decrease in the measured absorbance, the concentration of anti-HIV protease antibodies in the serum or plasma is calculated.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A method for quantifying an HIV protease inhibitor in a sample, comprising:
   (a) combining an HIV protease, a conjugate comprising an HIV protease inhibitor analog, and a sample suspected of containing an HIV protease inhibitor, wherein the HIV protease is immobilized on a surface of a solid phase, wherein the conjugate comprises a carrier and at least two HIV protease inhibitor analogs linked to the carrier, wherein the carrier is selected from the group consisting of a protein, a polysaccharide, and a polymer, and wherein the HIV protease and the conjugate form a detectable complex;
   (b) measuring the amount of the detectable complex; and
   (c) relating the amount of the detectable complex to a concentration of the HIV protease inhibitor in the sample.

2. The method of claim 1, wherein the HIV protease inhibitor comprises a member selected from the group consisting of an HIV protease inhibitor compound, an anti-HIV protease antibody, and a metabolite of an HIV protease inhibitor compound.

3. The method of claim 1, wherein the HIV protease inhibitor comprises a member selected from the group consisting of amprenavir, indinavir, lopinavir, nelfinavir, ritonavir, and saquinavir.

4. The method of claim 1, wherein the HIV protease inhibitor analog comprises an amprenavir analog.

5. The method of claim 1, wherein the carrier comprises aminodextran.

6. The method of claim 1, wherein the conjugate comprises a label.

7. The method of claim 6, wherein the label comprises a member selected from the group consisting of a fluorescent label, a luminescent compound, a radioactive isotope, an electrochemiluminescent label, an enzyme, and an enzyme substrate.

8. The method of claim 6, wherein the label comprises a fluorescein.

9. The method of claim 1, wherein the sample is a biological sample.

10. The method of claim 9, wherein the biological sample comprises a member selected from the group consisting of human serum and human plasma.

11. The method of claim 1, wherein the HIV protease comprises HIV-1 protease.

12. The method of claim 1, wherein the HIV protease is immobilized on the surface through adsorption.

13. The method of claim 1, wherein the HIV protease is immobilized on the surface through an interaction with an antibody.

14. The method of claim 1, wherein the HIV protease is immobilized on the surface through a covalent bond.

15. The method of claim 1, wherein the HIV protease is immobilized on the surface through binding of biotin with avidin or streptavidin.

16. The method of claim 1, wherein the conjugate comprises a carrier and at least two HIV protease inhibitor analogs linked to the carrier, and the measuring the amount of the detectable complex comprises measuring agglutination.

17. The method of claim 16, wherein the solid phase comprises a microparticle.

18. The method of claim 1, wherein the conjugate comprises a fluorescent label, and the measuring the amount of the detectable complex comprises measuring fluorescence polarization.

19. The method of claim 1, wherein the solid phase comprises a member selected from the group consisting of a particle, a microtiter plate, a cuvette, a tube, and a strip.

20. The method of claim 19, further comprising separating the solid phase from the sample prior to measuring the amount of the detectable complex.

21. The method of claim 20, wherein the measuring the amount of the detectable complex comprises measuring a spectroscopic property of the solid phase.

22. The method of claim 1, wherein the conjugate comprises biotin, and the method further includes immobilizing the detectable complex on a surface of a solid phase, the surface comprising avidin or streptavidin.

23. The method of claim 22, wherein the HIV protease is linked to a label.

24. The method of claim 23, wherein the label is an electrochemiluminescent label.

25. A method for quantifying an HIV protease inhibitor in a sample, comprising:
(a) combining an HIV protease, a conjugate comprising a carrier and at least two HIV protease inhibitor analogs linked to the carrier, and a sample suspected of containing an HIV protease inhibitor, wherein the HIV protease is immobilized on a surface of a microparticle, the HIV protease and the conjugate together undergo agglutination, and the sample is human serum or human plasma;
(b) measuring the agglutination; and
(c) relating the amount of agglutination to a concentration of the HIV protease inhibitor in the sample.

26. A method for quantifying an HIV protease inhibitor in a sample, comprising:
(a) combining a multivalent carrier comprising at least two HIV protease enzymes, a conjugate comprising a microparticle and an HIV protease inhibitor analog, and a sample suspected of containing an HIV protease inhibitor, wherein the HIV protease and the conjugate together undergo agglutination, and the sample is human serum or human plasma;
(b) measuring the agglutination; and
(c) relating the amount of agglutination to a concentration of the HIV protease inhibitor in the sample.

27. A kit for quantifying an HIV protease inhibitor in a sample, comprising:
(a) HIV protease immobilized on a surface of a solid phase; and
(b) a conjugate comprising an HIV protease inhibitor analog, wherein the conjugate comprises a carrier and at least two HIV protease inhibitor analogs linked to the carrier, and the carrier is selected from the group consisting of a protein, a polysaccharide, and a polymer.

28. The kit of claim 27, wherein the HIV protease inhibitor analog comprises an analog of a member selected from the group consisting of an HIV protease inhibitor compound, an anti-HIV protease antibody, and a metabolite of an HIV protease inhibitor compound.

29. The kit of claim 27, wherein the HIV protease inhibitor analog comprises a member selected from the group consisting of an amprenavir analog, an indinavir analog, a lopinavir analog, a nelfinavir analog, a ritonavir analog, or a saquinavir analog.

30. The kit of claim 27, wherein the carrier comprises aminodextran.

31. The kit of claim 27, wherein the conjugate comprises a label selected from the group consisting of a fluorescent label, a luminescent compound, a radioactive isotope, an electrochemiluminescent label, an enzyme, and an enzyme substrate.

32. The kit of claim 31, wherein the label comprises a fluorescein.

33. The kit of claim 27, wherein the conjugate comprises a microparticle, and at least two HIV protease inhibitor analogs linked to the microparticle.

34. The kit of claim 33, wherein at least two HIV protease enzymes are linked to a multivalent carrier.

35. The kit of claim 27, wherein the HIV protease comprises HIV-1 protease.

36. The kit of claim 27, wherein the HIV protease is immobilized on the surface through adsorption.

37. The kit of claim 27, wherein the HIV protease is immobilized on the surface through an interaction with an antibody.

38. The kit of claim 27, wherein the HIV protease is immobilized on the surface through a covalent bond.

39. The kit of claim 27, wherein the HIV protease is immobilized an the surface through binding of biotin with avidin or streptavidin.

40. The kit of claim 27, wherein the solid phase comprises a member selected from the group consisting of a particle, a microtiter plate, a cuvette, a tube, and a strip.

41. The kit of claim 27, wherein the solid phase comprises a microparticle.

42. The kit of claim 27, further comprising calibrating material.

* * * * *